United States Patent
Menegatti

(10) Patent No.: US 10,065,988 B2
(45) Date of Patent: Sep. 4, 2018

(54) PEPTOID AFFINITY LIGANDS

(71) Applicant: Stefano Menegatti, Raleigh, NC (US)

(72) Inventor: Stefano Menegatti, Raleigh, NC (US)

(73) Assignee: Stefano Menegatti, Raleigh, NC (US)

( * ) Notice: Subject to any disclaimer, the term of this patent is extended or adjusted under 35 U.S.C. 154(b) by 0 days.

(21) Appl. No.: 14/949,800

(22) Filed: Nov. 23, 2015

(65) Prior Publication Data

US 2016/0075734 A1    Mar. 17, 2016

Related U.S. Application Data

(63) Continuation-in-part of application No. PCT/US2014/039995, filed on May 29, 2014.

(60) Provisional application No. 62/084,383, filed on Nov. 25, 2014, provisional application No. 61/829,712, filed on May 31, 2013.

(51) Int. Cl.
| | |
|---|---|
| *C07K 7/06* | (2006.01) |
| *C07K 1/22* | (2006.01) |
| *C07K 16/00* | (2006.01) |
| *B01J 20/26* | (2006.01) |
| *B01J 20/24* | (2006.01) |
| *B01J 20/286* | (2006.01) |
| *C07K 1/107* | (2006.01) |
| *C07K 5/103* | (2006.01) |

(52) U.S. Cl.
CPC ............ *C07K 1/22* (2013.01); *B01J 20/24* (2013.01); *B01J 20/261* (2013.01); *B01J 20/286* (2013.01); *C07K 1/1077* (2013.01); *C07K 5/1008* (2013.01); *C07K 7/06* (2013.01); *C07K 16/00* (2013.01)

(58) Field of Classification Search
None
See application file for complete search history.

(56) References Cited

U.S. PATENT DOCUMENTS

2016/0159859 A1* 6/2016 Menegatti ............ C07K 16/065
530/329

FOREIGN PATENT DOCUMENTS

| EP | 3004136 B1 | 4/2017 |
| WO | WO 2013049830 | * 4/2013 |

OTHER PUBLICATIONS

Chongsiriwatana, Nathaniel P. et al, "Peptoids that mimic the structure, function, and mechanism of helical antimicropal peptides." PNAS (2008) 105(8) p. 2794-2799.*

Mallik, Rangan et al, "Development of sulfhydryl-reactive silica for protein immobilization in high-performance affinity chromatography." Anal. Chem. (2007) 79 p. 1411-1424.*

The Macherey-Nagel catalog page describing Nucleosil HPLC resins, http://www.mn-net.com/tabid/6121/default.aspx, downloaded Jan. 23, 2017.*

Yampolsky, Lev Y. and Stoltzfus, Arlin, "The exchgangeability of amino acids in proteins." Genetics (2005) 170 p. 1459-1472.*

Dhanalakshmi et al. "Rhodium catalysed coupling reaction of myrcene with ethyl acetoacetate in the ionic liquid 1-ethyl-3-methylimidazolium triflimide" *Tetrahedron* 59:9907-9911 (2003).

Haigh et al. "Affinity ligands for immunoglobulins based on the multicomponent Ugi reaction" *Journal of Chromatography B* 877:1440-1452 (2009).

International Search Report and the Written Opinion of the International Searching Authority corresponding to International Patent Application No. PCT/US2014/039995 (8 pages) (dated Sep. 30, 2014).

Menegatti et al. "Purification of polyclonal antibodies from Cohn fraction II + III, skim milk, and whey by peptide ligand" *Journal of Separation Sciences* 35:3139-3148 (2012).

Brown et al. "Biomimicry of surfactant protein C" *Accounts of Chemical Research* 41(10):1409-1417 (2008).

Burkoth et al. "Incorporation of Unprotected Heterocyclic Side Chains into Peptoid Oligomers via Solid-Phase Submonomer Synthesis" *Journal of the American Chemical Society* 125:8841-8845 (2003).

Chongsiriwatana et al. "Peptoids that mimic the structure, function, and mechanism of helical antimicrobial peptides" *Proceedings of the National Academy of Sciences* 105(8):2794-2799 (2008).

Drexler, Eric K. "Peptoids at the 7th Summit: Toward Macromolecular Systems Engineering" *Peptide Science* 96:537-544 (2011).

Fara et al. "Microwave-assisted coupling with DIC/HOBt for the synthesis of difficult peptoids and fluorescently labeled peptides—a gentle heat goes a long way" *Tetrahedron Letters* 47:1011-1014 (2006).

(Continued)

*Primary Examiner* — Fred H Reynolds
(74) *Attorney, Agent, or Firm* — Jenkins, Wilson, Taylor & Hunt, P.A.

(57) ABSTRACT

Compounds of Formulas I:

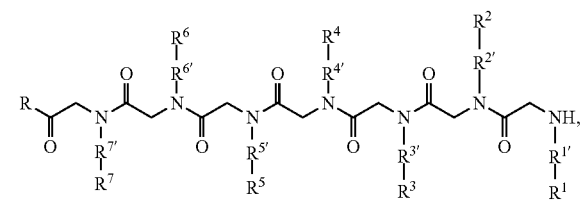

and shorter variants thereof are described, along with solid supports having such compounds coupled thereto, and the use thereof as affinity ligands for antibodies.

8 Claims, 5 Drawing Sheets

(56) References Cited

OTHER PUBLICATIONS

Gorske et al. "Local and Tunable n→π* Interactions Regulate Amide Isomerism in the Peptoid Backbone" *Journal of the American Chemical Society* 129:8928-8929 (2007).
Guichard, Gilles "β-Peptides, γ-Peptides and Isosteric Backbones: New Scaffolds with Controlled Shapes for Mimicking Protein Secondary Structure Elements" *Pseudo-Peptides in Drug Development* Chapter 2 (pp. 33-120) (2005).
Hara et al. "Probing the Structural Requirements of Peptoids That Inhibit HDM2—p53 Interactions" *Journal of the American Chemical Society* 128:1995-2004 (1995).
Haynes et al. "Comblike, Monodisperse Polypeptoid Drag-Tags for DNA Separations by End-Labeled Free-Solution Electrophoresis (ELFSE)" *Bioconjugate Chemistry* 16:929-938 (2005).
Huang et al. "Biomimetic peptoid oligomers as dual-action antifreeze agents" *Proceedings of the National Academy of Sciences* 109(49):19922-19927 (2012).
International Preliminary Report on Patentability corresponding to International Patent Application No. PCT/US2014/039995 (5 pages) (dated Dec. 1, 2015).
Kirshenbaum et al. "Sequence-specific polypeptoids: A diverse family of heteropolymers with stable secondary structure" *Proceedings of the National Academy of Sciences USA* 95:4303-4308 (1998).
Kwon et al. "Quantitative Evaluation of the Relative Cell Permeability of Peptoids and Peptides" *Journal of the American Chemical Society* 129:1508-1509 (2007).
Maayan et al. "Folded biomimetic oligomers for enantioselective catalysis" *Proceedings of the National Academy of Sciences* 106(33):13679-13684 (2009).
Miller et al. "Comparison of the Proteolytic Susceptibilities of Homologous L-Amino Acid, D-Amino Acid, and N-Substituted Glycine Peptide and Peptoid Oligomers" *Drug Development Research* 35:20-32 (1995).
Mora et al. "Identification from a Positional Scanning Peptoid Library of in Vivo Active Compounds That Neutralize Bacterial Endotoxins" *Journal of Medicinal Chemistry* 48:1265-1268 (2005).
Murphy et al. "A combinatorial approach to the discovery of efficient cationic peptoid reagents for gene delivery" *Proceedings of the National Academy of Sciences USA* 95:1517-1522 (1998).
Nam et al. "Free-floating ultrathin two-dimensional crystals from sequence-specific peptoid polymers" *Nature Materials* 9:454-460 (2010).
Nguyen et al. "Improving SH3 domain ligand selectivity using a non-natural scaffold" *Chemistry & Biology* 7:463-473 (2000).
Olivos et al. "Microwave-Assisted Solid-Phase Synthesis of Peptoids" *Organic Letters* 4(23):4057-4059 (2002).
Park et al. "Structural and Dynamical Characteristics of Peptoid Oligomers with Achiral Aliphatic Side Chains Studied by Molecular Dynamics Simulation" *The Journal of Physical Chemistry B* 115:10967-10975 (2011).
Patch et al. "Helical Peptoid Mimics of Magainin-2 Amide" *Journal of the American Chemical Society* 125:12092-12093 (2003).
Patch et al. "Versatile Oligo(N-Substituted) Glycines: The Many Roles of Peptoids in Drug Discovery" *Pseudo-peptides in Drug Discovery* Chapter 1 (pp. 1-31) (2004).
Peretto et al. "Cell penetrable peptoid carrier vehicles: synthesis and evaluation" *Chemical Communications* 18:2312-2313 (2003).
Pirrung et al. "[19]F-Encoded Combinatorial Libraries: Discovery of Selective Metal Binding and Catalytic Peptoids" *Journal of Combinatorial Chemistry* 4:329-344 (2002).
Reddy et al. "Protein 'fingerprinting' in complex mixtures with peptoid microarrays" *Proceedings of the National Academy of Sciences* 102(36):12672-12677 (2005).
Reddy et al. "Identification of Candidate IgG Biomarkers for Alzheimer's Disease via Combinatorial Library Screening" *Cell* 144:132-142 (2011).
Sanborn et al. "Extreme Stability of Helices Formed by Water-Soluble Poly-N-Substituted Glycines (Polypeptoids) with α-Chiral Side Chains" *Biopolymers* 63:12-20 (2002).
Schröder et al. "Peptoidic Amino- and Guanidinium-Carrier Systems: Targeted Drug Delivery into the Cell Cytosol or the Nucleus" *Journal of Medicinal Chemistry* 51:376-379 (2008).
Shah et al. "Oligo(N-aryl glycines): A New Twist on Structured Peptoids" *Journal of the American Chemical Society* 130:16622-16632 (2008).
Statz et al. "Surface-immobilized antimicrobial peptoids" *Biofouling* 24(6):439-448 (2008).
Statz et al. "Experimental and Theoretical Investigation of Chain Length and Surface Coverage on Fouling of Surface Grafted Polypeptoids" *Biointerphases* 4(2):FA22-FA32 (2009).
Wender et al. "The design, synthesis, and evaluation of molecules that enable or enhance cellular uptake: Peptoid molecular transporters" *Proceedings of the National Academy of Sciences* 97(24):13003-13008 (2000).
Wu et al. "Helical Peptoid Mimics of Lung Surfactant Protein C" *Chemistry & Biology* 10:1057-1063 (2003).
Zuckermann et al. "Efficient Method for the Preparation of Peptoids [Oligo(N-substituted glycines)] by Submonomer Solid-Phase Synthesis" *Journal of the American Chemical Society* 114:10646-10647 (1992).
Zuckermann et al. "Discovery of Nanomolar Ligands for 7-Transmembrane G-Protein-Coupled Receptors from a Diverse N-(Substituted)glycine Peptoid Library" *Journal of Medicinal Chemistry* 37:2678-2685 (1994).
Intent to Grant for European Patent Application No. 14733870.1 dated Oct. 24, 2016.
Grant Decision for European Patent Application No. 14733870.1 dated Mar. 16, 2017.
Heine et al., "Synthesis and screening of peptoid arrays on cellulose membranes," Tetrahedron, 59, pp. 9919-9930 (2003). first page only.
Chinese Office Action for Chinese Application No. 201480030558.2 dated Jun. 19, 2018.

* cited by examiner

PEPTOID AFFINITY LIGANDS

RELATED APPLICATION DATA

This application claims the benefit of and priority from U.S. Provisional Patent Application No. 62/084,383, filed on Nov. 25, 2014, and is a continuation-in-part of International Application No. PCT/US2014/039995, filed on May 29, 2014, which claims the benefit of and priority from U.S. Provisional Patent Application No. 61/829,712, filed on May 31, 2013, the disclosures of each of which are incorporated herein by reference in their entirety.

BACKGROUND OF THE INVENTION

Monoclonal antibodies and Fc-fusion proteins have emerged as an important class of therapeutic proteins for the treatment of a number of unmet diseases such as cancer, autoimmune diseases, immunodeficiency, skin disorders and neurological disorders. These products account for 40% of the overall pharmaceutical market with a volume of $35 billion in 2011. However, therapies based on antibodies are very expensive to consumers. Their high price is due in part to the high cost of isolation and purification of these biomolecules. A major contribution to the purification costs results from the ubiquitous use of Protein A or Protein G affinity chromatography capture step. Despite their high selectivity for IgG, these protein ligands suffer from high cost and low chemical and biochemical stability. The average cost of Protein A/G—based chromatographic media ranges between $8,000-15,000 per liter of resin. Protein ligands show in general poor chemical resistance towards the alkaline (0.1-1.0 M NaOH) cleaning-in-place and sanitisation-in-place procedures periodically applied for the removal of contaminants and required by regulatory guidelines. Further, they are prone to proteolytic degradation by enzymes present in the feed. Both chemical and enzymatic agents can cause ligand degradation and leakage of ligand fragments from the resin, resulting in shorter column lifetime and potential presence of toxic and immunogenic leachates in the product mainstream.

SUMMARY OF THE INVENTION

Extensive research has been carried out in both industry and academia to discover inexpensive and robust ligands with high affinity and selectivity for antibodies. A variety of synthetic compounds, including triazinic scaffolds, amino acids and peptides have been proposed for the selection of affinity ligands for downstream processing of biotherapeutics. A class that has recently been considered for the design of affinity ligands is represented by peptoids. This class of compounds possesses ideal characteristics for such application. First, the display of functional groups on peptoids resembles that of peptides, implying that peptoids can be designed or selected with levels of affinity and selectivity comparable to those of peptide ligands. Further, owing to the so-called "sub-monomer" protocol of synthesis, which employs primary amines, peptoids can explore a much wider chemical diversity than that available to protein ligands and peptides comprising natural amino acids. This enables fine tuning their composition to achieve higher target specificity and affinity. Finally, peptoids are completely resistant to proteolysis and are therefore advantageous for the purification of antibodies from fluids containing active enzymes, like whole plasma and its fractions or lysates of cell cultures, plants and other organisms.

Peptoids are therefore an economical alternative to Protein A. Besides the purification of biopharmaceuticals, these ligands can find further applications in areas such as diagnostics and process control. To the best of our knowledge, peptoid ligands have not been suggested for the purification of immunoglobulins, and IgG in particular.

Accordingly, a first aspect of the invention is a peptoid ligand that specifically binds to an antibody such as IgG, and/or an antibody Fc fragment, and/or an Fc-fusion protein. Such peptoid ligands are in some embodiments from 4 to 7 residues or monomers in length. Such peptoid ligands are optionally, but in some embodiments preferably, coupled to a solid support.

A further aspect of the invention is a method of binding an antibody, or antibody Fc fragment, or an Fc-fusion protein from a liquid composition containing the same, comprising the steps of: (a) providing a solid support comprising a peptoid ligand bound thereto as described herein, (b) contacting said composition to said solid support so that antibody or Fc fragments bind to said compound; and (c) separating said liquid composition from said solid support, with said antibody or Fc fragment bound to said solid support.

The foregoing and other objects and aspects of the present invention are explained in detail in the specification set forth below.

DETAILED DESCRIPTION OF ILLUSTRATIVE EMBODIMENTS

Figure 1:
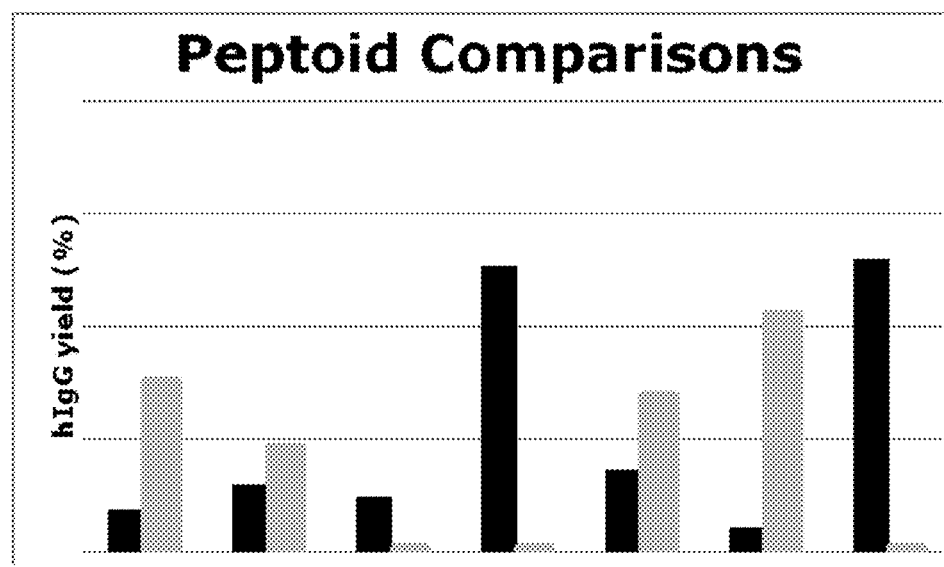
FIG. 1. Batch mode IgG adsorption to Toyopearl AF-amino 650 M resins functionalized with different peptoid ligands. IgG in the flow-through fractions (black) indicate the percent hIgG that was not adsorbed to the resin relative to the mass of hIgG loaded. The elution fractions (grey) indicate the percent of human IgG that was bound in phosphate buffered saline (PBS) and eluted (0.1 M glycine, pH 2.5) relative to the initial concentration of IgG that was loaded. Concentrations of hIgG in all fractions were determined by ELISA. The unmodified resin served as the negative control. Binding trials were done in duplicate for each resin.

The present invention now will be described more fully hereinafter with reference to the accompanying figures, in which embodiments of the invention are shown. This invention may, however, be embodied in many alternate forms and should not be construed as limited to the embodiments set forth herein. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

1. Definitions.

Functional group as used herein may be any suitable group or substituent, including but not limited to H, linear and cyclic alkyl, alkenyl, and alkynyl, possibly substituted and/or functionalized with groups such as alkoxy, halo, mercapto, azido, cyano, formyl, carboxyl, hydroxyl, nitro, acyl, aryloxy, alkylthio, amino, alkylamino, arylalkylamino, substituted amino, acylamino, acyloxy, ester, thioester, carboxylic thioester, ether, amide, amidino, sulfate, sulfoxyl, sulfonyl, sulfonyl, sulfonic acid, sulfonamide, urea, alkoxylacylamino, aminoacyloxy, guanidino, aldehyde, keto, imine, nitrile, phosphate, thiol, epoxide, peroxide, thiocyanate, amidine, oxime, nitrile, diazo, etc., these terms including combinations of these groups (e.g. alkylated groups) as discussed further below.

"Alkyl" as used herein alone or as part of another group, refers to a straight, branched chain, or cyclic, saturated or unsaturated, hydrocarbon containing from 1 or 2 to 10 or 20 carbon atoms, or more. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Alkyl may be saturated or unsaturated and hence the term "alkyl" as used herein is inclusive of alkenyl and alkynyl when the alkyl substituent contains one or more unsaturated bond (for example, one or two double or triple bonds). The alkyl group may optionally contain one or more heteroatoms (e.g., one, two, or three or more heteroatoms independently selected from O, S, and NR', where R' is any suitable substituent such as described immediately above for alkyl substituents), to form a linear heteroalkyl or heterocyclic group as specifically described below.

"Alkenyl" as used herein refers to an alkyl group as described above containing at least one double bond between two carbon atoms therein.

"Alkynyl" as used herein refers to an alkyl group as described above containing at least one triple bond between two carbon atoms therein.

"Alkylene" as used herein refers to an alkyl group as described above, with one terminal hydrogen removed to form a bivalent substituent.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical or a —N(R$_a$)C(O)R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Solid support" as used herein may comprise any suitable material, including organic materials (e.g., organic polymers), metals (e.g., titanium), inorganic materials (e.g., silica) and composites thereof. The solid supports may be in any suitable shape or form, including films, receptacles such as microtiter plate wells (e.g., floors and/or walls thereof) particles (e.g., beads formed from natural or synthetic polymers, inorganic materials such as glass or silica, composites thereof, etc.) such as for chromatography column packings, etc.

"Coupling group" as used herein may be any suitable reactive group, e.g., an alkene, alkyne, alcohol, thiol, selenyl, phosphono, carboxylic acid, formyl, halide or amine group, displayed directly by the parent molecule or by means of an intervening linker group (e.g., an aliphatic, aromatic, or mixed aliphatic/aromatic group such as an alkyl, aryl, arylalkyl, or alkylarylalkyl group, etc.).

2. Compounds.

Compounds useful for carrying out the present invention include compounds of Formulas I-IV:

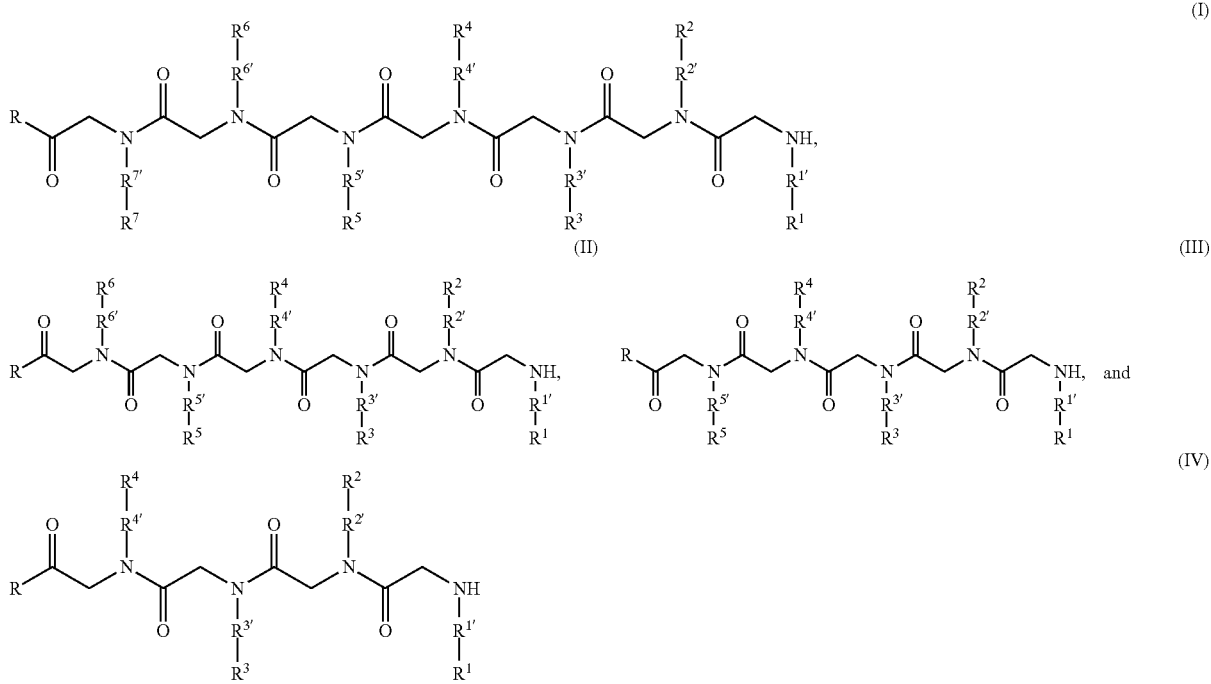

wherein:

R is a linking moiety (e.g., R is —OH, —NH$_2$, —NHR", —OR", —O—O—R", etc., where R' is alkyl, etc.) or —Z—R', where Z is a linking group and R' is a solid support (e.g., Z is —O—, —NH—, —O—NH—, —O—R"—S—, —NH—R"—S—, —O—NH—R"—S—, —O—R"—S—S—, —NH—R"—S—S—, —O—NH—R"—S—S—; ether (—O—), thioether (—S—), thioester, carbamate, carbonate, amide, ester, secondary/tertiary amine (e.g., obtained through a reductive amination coupling reaction), alkyl (e.g., obtained through a metathesis coupling reaction), alkenyl, phosphodiester, phosphoether, oxime, imine, hydrazone, acetal, hemiacetal, semicarbazone, ketone, ketene, aminal, hemiaminal, enamine, enol, disulphide, sulfone, etc.);

$R^{1'}$, $R^{2'}$, $R^{3'}$, $R^{4'}$, $R^{5'}$, $R^{6'}$, and $R^{7'}$ are each independently a C1 to C4 alkyl chain;

$R^1$ is a basic group, such as a basic aromatic group, examples of which include but are not limited to pyridinyl-, quinolinyl- and isoquinolinyl-, acridinyl-, pyrazinyl-, quinoxalinyl-, imidazolyl-, benzimidazolyl-, purinyl-, pyrazolyl-, indazolyl-, pyrimidinyl-, quinazolinyl-, pyridazinyl-, cinnolinyl-, and the like;

$R^2$ is an aromatic group, examples of which include but are not limited to (a) non-substituted, e.g. phenyl-, benzyl-, naphtalyl-, and related groups or derivatives thereof; or (b) substituted, e.g. indolyl-, and related groups or derivatives thereof; and (c) derivatives of the foregoing obtained by functionalization, e.g. hydroxylation, amination, carboxylation, and the like, alkylation, alkenylation, alkinylation, and the like, and derivatives thereof;

$R^3$ is a basic group, such as a basic aliphatic group, examples of which include but are not limited to comprising but not limited to the group of primary, secondary, tertiary and quaternary amine, guanidinyl-, and related groups; or an hydrophilic moiety capable of forming hydrogen bonds, e.g. carbamoyl-, hydroxyl-, urea, and the like;

$R^4$ is Hydrogen (or also for compounds of Formula IV, an aliphatic group, an aromatic group, an acidic group, a hydrophilic group, a basic group, or coupling group).

$R^5$ is an aromatic group, a basic group, or a basic aromatic group, such as defined for $R^1$ and $R^2$ above (or also for compounds of Formula III, an aliphatic group, an an acidic group, a hydrophilic group, or coupling group), $R^6$ is Hydrogen, or an acidic group such as a carboxyl group, a sulfonate group, etc (or also for compounds of Formula II, an aliphatic group, an aromatic group, a hydrophilic group, a basic group, or coupling group);

$R^7$ is Hydrogen, or any of the groups given in connection with $R^1$ through $R^6$ above, or a coupling group group suitable for covalently coupling the peptoid ligand with another (a) natural, e.g. a protein, a polynucleotide, a lipid, a peptide, and derivatives thereof, or (b) synthetic compound, e.g. a drug, an organic compound, a metallorganic compound, an inorganic compound, or (c) a surface, e.g. a chromatographic resin, a membrane, a metal surface, a fiber, a self-assembled structure, or derivatives thereof.

In some embodiments the solid support comprises a particle (e.g., a porous polymer bead like a pearl of chromatographic resin).

In some embodiments the solid support comprises an inorganic material (e.g., silica, titania, zirconia, and the like).

In some embodiments, the solid support comprises an organic polymer material (e.g., polyethersulfone, PMMA, etc.).

"Coupling group" in a compound as described herein above or below may be independently selected from: (i) a linking moiety (e.g., R is —OH, —NH$_2$, —NHR", —OR", —O—O—R", etc., where R' is alkyl, etc.) or (ii) —Z—R', where Z is a linking group and R' is a solid support (e.g., Z is —O—, —NH—, —O—NH—, —O—R"—S—, —NH—R"—S—, —O—NH—R"—S—, —O—R"—S—S—, —NH—R"—S—S—, —O—NH—R"—S—S—; ether (—O—), thioether (—S—), thioester, carbamate, carbonate, amide, ester, secondary/tertiary amine (e.g., obtained through a reductive amination coupling reaction), alkyl (e.g., obtained through a metathesis coupling reaction), alkenyl, phosphodiester, phosphoether, oxime, imine, hydrazone, acetal, hemiacetal, semicarbazone, ketone, ketene, aminal, hemiaminal, enamine, enol, disulphide, sulfone, etc.);

Peptoid compounds of the present invention such as compounds of Formulas I-IV can be prepared in accordance with known techniques, including but not limited to those described in: N. J. Brown, J. Johansson, and A. E. Barron, Acc. Chem. Res. 41, 1409-1417 (2008); N. P. Chongsiriwatana, J. A. Patch, A. M. Czyzewski, M. T. Dohm, A. Ivankin, D. Gidalevitz, R. N. Zuckermann, and A. E. Barron, PNAS 105, 2794-2799 (2008); K. E. Drexler, Peptide Science 96, 537-544 (2011); B. C. Gorske, B. L. Bastian, G. D. Geske, and H. E. Blackwell, J. Am. Chem. Soc. 129, 8928-8929 (2007); T. Hara, S. R. Durell, M. C. Myers, and D. H. Appella, J. Am. Chem. Soc. 128, 1995-2004 (2006); R. D. Haynes, R. J. Meagher, J.-I. Won, F. M. Bogdan, and A. E. Barron, Bioconjugate Chem. 16, 929-938 (2005); K. Kirshenbaum, A. E. Barron, R. A. Goldsmith, P. Armand, E. K. Bradley, K. T. V. Truong, K. A. Dill, F. E. Cohen, and R. N. Zuckermann, PNAS 95, 4303-4308 (1998); Y.-U. Kwon and T. Kodadek, J. Am. Chem. Soc. 129, 1508-1509 (2007); G. Maayan, M. D. Ward, and K. Kirshenbaum, PNAS 106, 13679-13684 (2009); S. M. Miller, R. J. Simon, S. Ng, R. N. Zuckermann, J. M. Kerr, and W. H. Moos, Drug Development Research 35, 20-32 (1995); P. Mora, I. Masip, N. Cortés, R. Marquina, R. Merino, J. Merino, T. Carbonell, I. Mingarro, A. Messeguer, and E. Pérez-Payá, J. Med. Chem. 48, 1265-1268 (2005); J. E. Murphy, T. Uno, J. D. Hamer, F. E. Cohen, V. Dwarki, and R. N. Zuckermann, PNAS 95, 1517-1522 (1998); K. T. Nam, S. A. Shelby, P. H. Choi, A. B. Marciel, R. Chen, L. Tan, T. K. Chu, R. A. Mesch, B.-C. Lee, M. D. Connolly, C. Kisielowski, and R. N. Zuckermann, Nature Materials 9, 454-460 (2010); J. T. Nguyen, M. Porter, M. Amoui, W. T. Miller, R. N. Zuckermann, and W. A. Lim, Chem. Biol. 7, 463-473 (2000); P. E. Nielsen, ed., Pseudo-peptides in Drug Discovery, 1st ed. (Wiley-VCH, 2004); S. H. Park and I. Szleifer, J. Phys. Chem. B 115, 10967-10975 (2011); J. A. Patch and A. E. Barron, J. Am. Chem. Soc. 125, 12092-12093 (2003); I. Peretto, R. M. Sanchez-Martin, X. Wang, J. Ellard, S. Mittoo, and M. Bradley, Chem. Commun. 2312-2313 (n.d.); M. C. Pirrung, K. Park, and L. N. Tumey, J. Comb. Chem. 4, 329-344 (2002); M. M. Reddy and T. Kodadek, Proc. Nat. Acad. Sci. USA 102, 12672-12677 (2005); M. M. Reddy, R. Wilson, J. Wilson, S. Connell, A. Gocke, L. Hynan, D. German, and T. Kodadek, Cell 144, 132-142 (2011); T. J. Sanborn, C. W. Wu, R. N. Zuckermann, and A. E. Barron, Biopolymers 63, 12-20 (2002); T. Schröder, N. Niemeier, S. Afonin, A. S. Ulrich, H. F. Krug, and S. Bräse, J. Med. Chem. 51, 376-379 (2008); N. H. Shah, G. L. Butterfoss, K. Nguyen, B. Yoo, R. Bonneau, D. L. Rabenstein, and K. Kirshenbaum, J. Am. Chem. Soc. 130, 16622-16632 (2008); A. Statz, J. Kuang, C. Ren, A. Barron, I. Szleifer, and P. Messersmith, Biointerphases 4, FA22-FA32 (2009); A. R. Statz, J. P. Park, N. P. Chongsiriwatana, A. E. Barron, and P. B. Messersmith, Biofouling 24, 439-448 (2008); P. A. Wender, D. J. Mitchell, K. Pattabiraman, E. T. Pelkey, L. Steinman, and J. B. Rothbard, Proc. Nat. Acad. Sci. USA 97, 13003-13008 (2000); C. W. Wu, S. L. Seurynck, K. Y. C. Lee, and A. E. Barron, Chem. Biol. 10, 1057-1063 (2003); R. N. Zuckermann, J. M. Kerr, S. B. H. Kent, and W. H. Moos, J. Am. Chem. Soc. 114, 10646-10647 (1992); R. N. Zuckermann, E. J. Martin, D. C. Spellmeyer, G. B. Stauber, K. R. Shoemaker, J. M. Kerr, G. M. Figliozzi, D. A. Goff, and M. A. Siani, J. Med. Chem. 37, 2678-2685 (1994).

B. Methods of Use.

The peptoids of the present invention may be used to bind to, collect, purify, immobilise on a solid surface, etc., any type of antibody or antibody fragment (e.g., Fc fragments, Fab fragments, and scFV fragments), including both natural and recombinant (including chimeric) antibodies, engineered multibodies, single domain antibodies, and combinations thereof, such as divalent antibodies and camelid immunoglobulins, and both monoclonal and polyclonal antibodies, or an Fc-fusion protein. The antibodies may be of any species of origin, including mammalian (rabbit, mouse, rat, cow, goat, sheep, llama, camel, alpaca, etc), avian (e.g., chicken, turkey, etc.), shark, etc., including fragments, chimeras and combinations thereof as noted above. The antibodies may be of any type of immunoglobulin, including but not limited to IgG, IgA, IgE, IgD, IgM, IgY (avian), etc.

In some embodiments, the antibodies or Fc fragments (including fusion proteins thereof) are carried in a biological fluid such as blood or a blood fraction (e.g., blood sera, blood plasma), egg yolk and/or albumin, tissue or cell growth media, a tissue lysate or homogenate, etc.

Thus, as noted above, the present invention provides a method of binding an antibody or antibody Fc fragment from a liquid composition containing the same, comprising the steps of:

(a) providing a solid support comprising a compound as described above (b) contacting said composition to said solid support so that antibody or Fc fragment or Fc-fusion protein bind to said compound; and (c) separating said liquid composition from said solid support, with said antibody or Fc fragment or Fc-fusion protein bound to said solid support; and optionally (but in some embodiments preferably)

(d) separating said antibody or Fc fragment or Fc-fusion protein from said solid support.

The methods can be carried out in like manner to those employing protein A, or by variations thereof that will be apparent to those skilled in the art. For example, the contacting and separating steps can be carried out continuously, (e.g., by column chromatography), after which the separating step can then be carried out (e.g., by elution), in accordance with known techniques.

In some embodiments, such as when the liquid composition from which the antibodies or Fc fragments or Fc-fusion proteins are to be collected, comprises a biological fluid, the liquid composition further comprises at least one proteolytic enzyme. The peptoid binding ligands are advantageously resistant to degradation by proteolytic enzymes.

In addition, photoaffinity labelling of all the above mentioned target antibodies can be carried out by replacing any of the side-chain residues of the peptoid with a photoreactive group, such as a benzophenone group.

The present invention is explained in greater detail in the following non-limiting Examples.

EXAMPLE 1

Solid-Phase Synthesis of a Tetramer Peptoid Ligand and Use of the Resulting Affinity Adsorbent for the Purification of Human Polyclonal or Monoclonal Antibodies The selected groups, as numbered from the N- to the C-terminus, are: imidazoyl, indolyl-, guanidyl-, and methyl-. Correspondingly, the amines employed for the peptoid synthesis are respectively histamine, tryptamine, agmatine, and methylamine. Presented in Scheme 1, as follows:

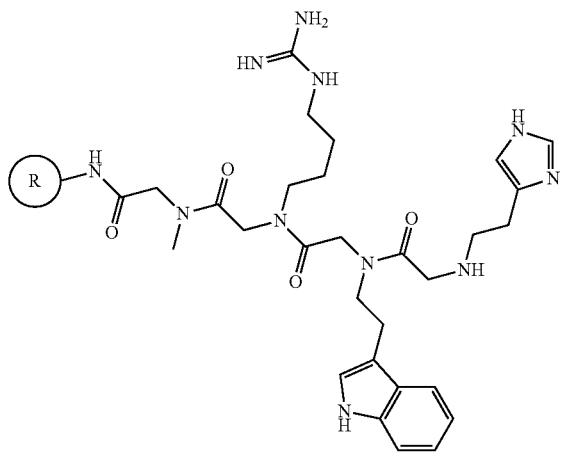

The chromatographic resin Toyopearl AF-Amino-650 M is chosen as solid support for synthesis. The synthesis comprises the following steps:

1. Coupling of bromoacetic acid in N,N'-dimethylformamide (DMF) via diisopropylcarbodiimide activation (hereafter referred to as DIC). Wash the resin with DMF and equilibrate with NMP.

2. Coupling of methylamine in N-methylpyrrolidone (NMP). Wash the resin with NMP and equilibrate with DMF.

3. Coupling of bromoacetic acid by DIC. Wash the resin with DMF and equilibrate with NMP.

4. Coupling of agmatine. Wash the resin with NMP and equilibrate with DMF.

5. Coupling of bromoacetic acid by DIC. Wash the resin with DMF and equilibrate with NMP.

6. Coupling of $N_{in}$-Boc-tryptamine. Wash the resin with NMP and equilibrate with DMF.

7. Coupling of bromoacetic acid by DIC. Wash the resin with DMF and equilibrate with NMP.

8. Coupling of $N_{im}$-Boc-histamine. Wash the resin with NMP, followed by DMF, and finally equilibrate the resin with DCM. Remove the Boc protecting groups by washing the resin two times with 75% TFA (trifluoroacetic acid) in DCM for 45 min, at room temperature. Wash the resin sequentially with DCM, DMF and DCM.

The resin is then vaccuum dried, packed in a chromatographic column, swollen in 20% v/v methanol in water, and equilibrated in phosphate buffer saline (PBS), pH 7.4.

A solution of human polyclonal IgG at 5 mg/mL in PBS is prepared and injected in the column at the linear velocity of 67 cm/h. After washing the column with 10 column volumes of equilibration buffer at the linear velocity of 200 cm/h, the bound antibody is eluted with 0.2 M Acetate buffer pH 4 at the linear velocity of 270 cm/h. The resin is finally regenerated with aqueous 0.1 M NaOH.

EXAMPLE 2

Preparation of Peptoids Directly to Amine-Containing Resin

Preparation Procedures: Peptoids were synthesized directly onto Toyopearl AF-amino 650 M resin (Tosoh Biosciences) at a 0.1 mmol/mL loading with a Biotage Alstra automated peptide synthesizer under microwave assistance using methods described previously (Fara et al. Tet. Lett. 2006 47, 1011-1014; Olivos et al. Org. Lett. 2002, 4(23), 4057-4059). The Fmoc-protected monomers for glycine, N-(-3-guanidinpropyl)glycine, N-(isobutyl)glycine, N-(3-(Boc-amino)-propyl)glycine and N-(benzyl)glycine were coupled to the peptoid using N,N,N',N'-Tetramethyl—O-(1H-benzotriazol-1-yl)uronium hexafluorophosphate (HBTU) with diisopropylethyl amine as the coupling agent in dimethyl formamide for 30 minutes at 50 C (Huang et al. PNAS 2012, 109(49), 19922-19927.). After coupling, the secondary amine was deprotected using 20% piperidine in DMF. The remaining residues were coupled to the peptoid sequence using a submonomer approach. Chloroacetic acid was coupled to the previous residue with diisopropylcarbodiimide (15 minutes, 75 C) followed by displacement of the chloride with the corresponding amine and potassium iodide as catalyst (1 hour, 50 C). The following amines were used in the halogen displacement step: 2-propylamine, histamine, and tryptamine (Zuckerman et al. J. AM. CHEM. SOC. 2003, 125, 8841). The ligands were deprotected directly on the resin using 90% trifluoroacetic acid, 5% triisopropylsilane, and 5% $H_2O$, followed by successive washing with triflouroacetic acid, methanol, and water.

Substituents on the immobilized peptoids are as given in Table 1 below, where the various "R" groups correspond to the Formulas above. The structure of the peptoids when free from (not covalently coupled to) a resin is given in Table 2 below.

TABLE 1

| ID | PV-P-G001 | PV-P-G003 | PV-P-G004 | PV-P-G005 | PV-P-G006 | PV-P-G012 |
|---|---|---|---|---|---|---|
| $R^1$ | -2-imidazole | -2-imidazole | -2-imidazole | -2-imidazole | -2-imidazole | -2-imidazole |
| $R^{1'}$ | —$CH_2CH_2$— | —$CH_2CH_2$— | —$CH_2CH_2$— | —$CH_2CH_2$— | —$CH_2CH_2$— | —$CH_2CH_2$— |
| $R^2$ | -3-indole | -3-indole | —$C_6H_5$ | -3-indole | —$C_6H_5$ | -3-indole |
| $R^{2'}$ | —$CH_2CH_2$— | —$CH_2CH_2$— | —$CH_2CH_2$— | —$CH_2CH_2$— | —$CH_2$— | —$CH_2CH_2$ |
| $R^3$ | —NH—(C=NH)—$NH_2$ (guanidyl) | —NH—(C=NH)—$NH_2$ (guanidyl) | —NH—(C=NH)—$NH_2$ (guanidyl) | —NH—(C=NH)—$NH_2$ (guanidyl) | —NH—(C=NH)—$NH_2$ (guanidyl) | —NH2 |
| $R^{3'}$ | —$CH_2CH_2CH_2$— | —$CH_2CH_2CH_2$— | —$CH_2CH_2CH_2$— | —$CH_2CH_2CH_2$— | —$CH_2CH_2CH_2$— | —$CH_2CH_2CH_2$— |
| $R^4$ | H | H | H | | | H |
| $R^{4'}$ | N/A | N/A | N/A | | | N/A |
| $R^5$ | —$CH_2CH_2$— | | | | | -3-indole |
| $R^{5'}$ | -3-indole | | | | | —$CH_2CH_2$— |
| $R^6$ | —$CH(CH_3)_2$ | | | | | —$CH(CH_3)_2$ |
| $R^{6'}$ | N/A | | | | | N/A |

TABLE 2

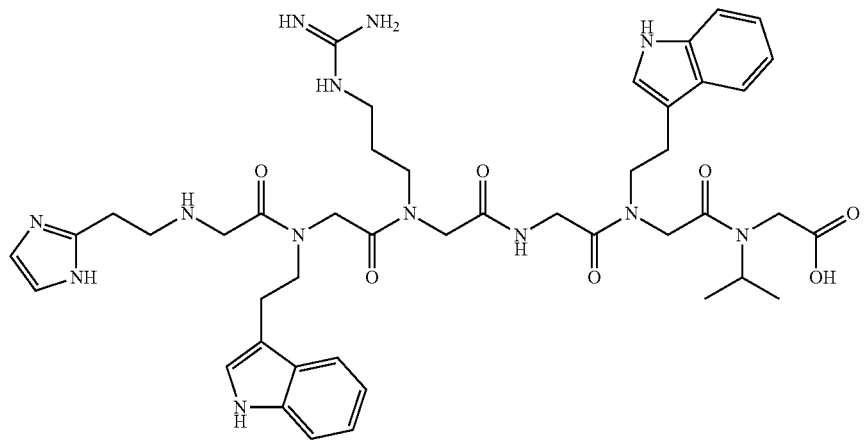 [SMILES: CC(C)N(CC(=O)O)C(=O)CN(CCc1c[nH]c2ccccc12)C(=O)CNC(=O)CN(CCCNC(=N)N)C(=O)CN(CCc1c[nH]c2ccccc12)C(=O)CNCCc1ncc[nH]1]

PV-P-G001

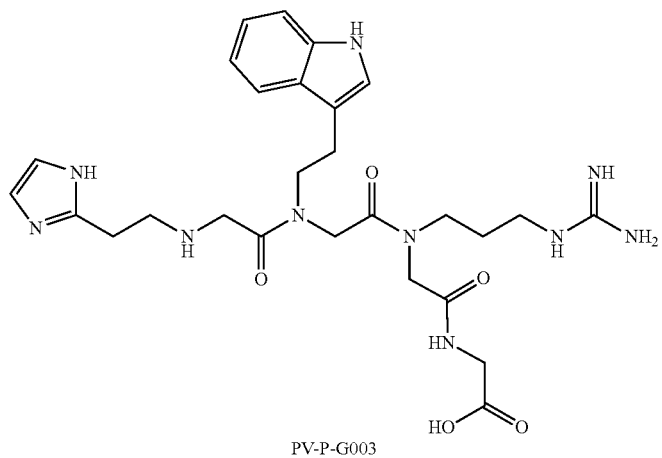

PV-P-G003

Figure 2:
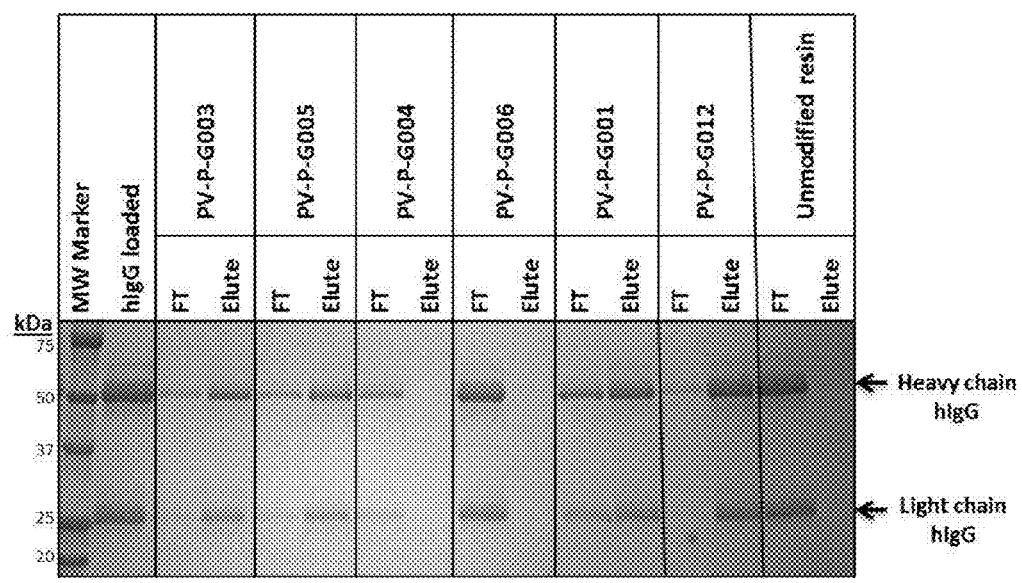
FIG. 2. Reducing SDS-PAGE analysis of elution and flow-through fractions from hIgG adsorption experiments. Lanes designated "FT" and "Elute" are the flow-through and elution fractions, respectively. The lane marked "hIgG loaded" is the pre-adsorbed hIgG solution that was incubated with each resin tested. The heavy and light chains of hIgG migrate at ~55 and ~25 kDa, respectively, on reducing SDS-PAGE gels. Bands observed in the flow-through represent hIgG that did not bind the resin, while bands observed in the elute represent hIgG that was adsorbed and subsequently eluted at low pH.

TABLE 2-continued
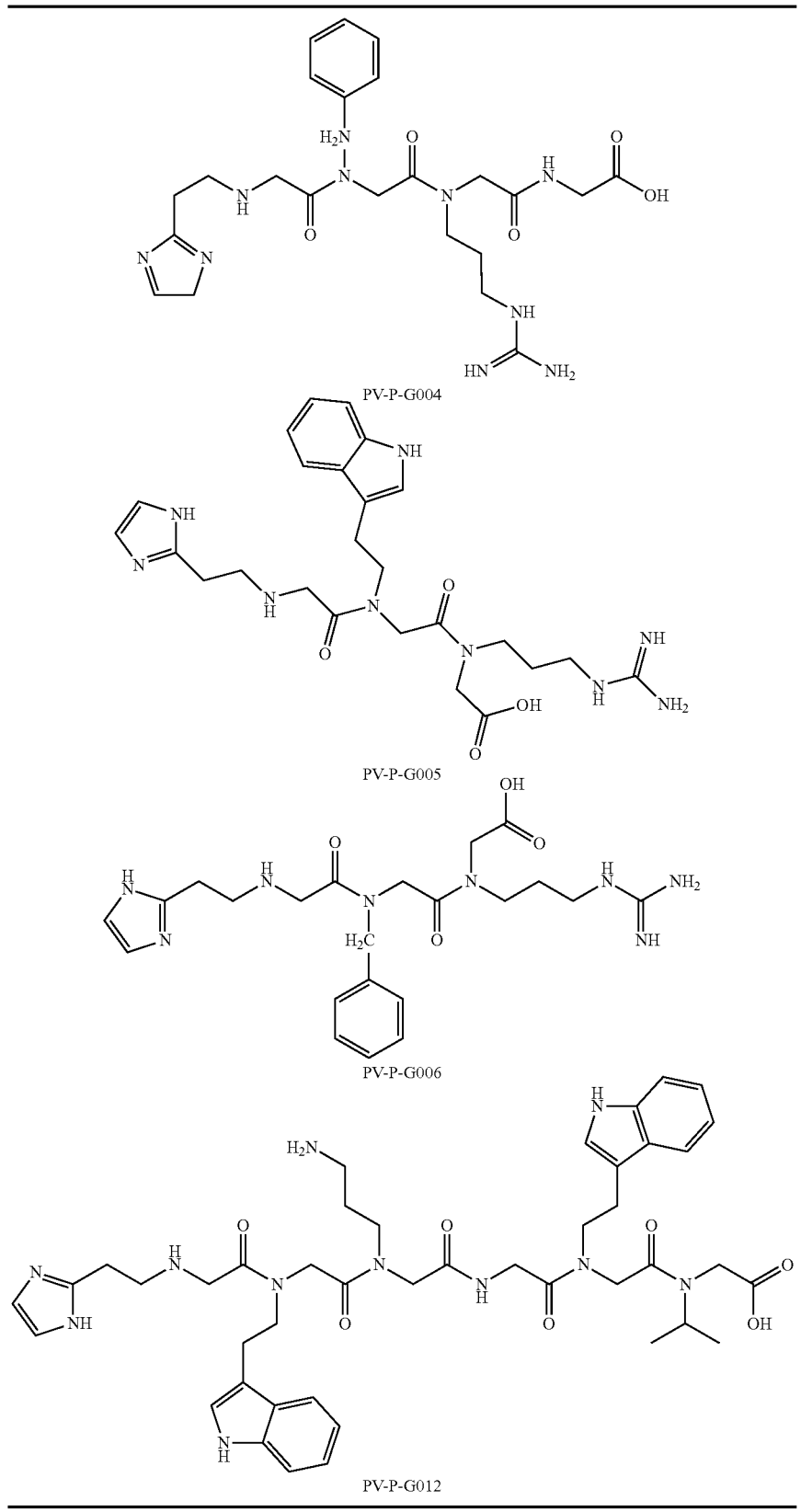
IgG Binding to Resin: The ability of the peptoid affinity ligands to bind human IgG (hIgG) was tested in batch mode. A 50% slurry of the resin was prepared, of which 200 µl (~100 mg resin) was transferred into the spin column. The resin was throughly washed with dH2O and equilibrated with PBS prior to hIgG exposure. Polyclonal hIgG (Equitech-Bio) was diluted to 0.5 mg/mL with PBS. After equilibration, a 0.5 mg/mL solution of hIgG was added to the resin to achieve a ratio of 2 mg hIgG per mL of resin, and allowed to incubate for 45 min at 22° C. with vigorous shaking. After incubation, the resin was centrifuged at 500×g for 2 min in which the filtrate of this step was collected and labeled as "flow-through" fraction. The resin was subsequently washed 2× with PBS. Elution buffer (0.1 M glycine, pH 2.5) was added to the resin and mixed vigorously for 10 min at 22° C. After centrifugation (500×g for 2 min) bound hIgG was eluted from the resin and collected in the filtrate. The amount of hIgG found in the flow-through and elution fraction was determined using an ELISA-based quantitative assay (Bethyl, Cat. No. E80-104). hIgG yields were determined as the ratio of hIgG mass in the elution fraction and hIgG mass in the loading solution (FIG. 1). SDS-PAGE analysis of all collected fractions was carried out to determine product purity and evaluate the ligand selectivity (FIG. 2). These data indicated that peptoids G001, G003, G005, and G012 were useful for binding IgG to the resin.

EXAMPLE 3

Preparation Procedures

Peptoids were produced using a Biotage Alstra automated peptide synthesizer under microwave assistance, using previously described methods (Fara et al. Tet. Lett. 2006 47, 1011-1014; Olivos et al. Org. Lett. 2002, 4(23), 4057-4059). The peptoids were synthesized on polystyrene-based resins for solid phase peptide synthesis (SPPS), including cysteamine 2-chlorotrityl resin and Fmoc-Rink amide resin. Prior to synthesis, the resin were swollen at 70° C. in DMF for 20 minutes. Fmoc-protected Rink resins were also pre-treated with 20% piperidine in DMF at room temperature to deprotect the resin. Amino acid residues, such as N-Fmoc-glycine and N-Fmoc-S-trityl-L-cysteine, were couple to the support using using diisopropylcarbodiimide (DIC) and Oxyma as coupling agent. Each coupling was performed in DMF at 75° C. for 5 minutes and followed by Fmoc-deprotection with 20% piperidine in DMF at room temperature. The other residues of the peptoid residues were added via conventional sub-monomer approach. First, bromoacetic acid was coupled using DIC in DMF at 40° C. for 15 minutes. Then, the appropriate primary amine is added via nucleophilic displacement of the terminal bromide in DMF at 60° C. for 15 minutes. When needed, protected diamines were used to allow the peptoid to be further functionalized after synthesis of the full sequence. Orthogonal protecting groups were chosen to survive the conditions of the peptoid synthesis, but deprotect during cleavage of the completed peptoid from the synthesis resin. The amines used for in examples herein were: n-propylamine, tryptamine, mono(tert-butylcarbamoyl)propananediamine, histamine, and 3-picolylamine. The sequences initially synthesised with a 3-aminopropyl residue in 3rd position were converted into a guandinyl group after conjugation to the chromatography resin The peptoids were cleaved from the synthesis resin using a mixture of trifluoroacetic acid, phenol, water, and triisopropylsilane (92.5/2.5/2.5/2.5). The crude peptoid was precipitated in ether, and then purified with low pressure reverse phase chromatography (C18, 10%-100% Acetonitrile/Water gradient with 0.1% acetic acid). The purified peptoid was lyophilized to a dry powder, and the mass of the product was confirmed with LC/MS. The peptoids synthesized for conjugation to chromatographic resin are shown in Table 3.

The affinity adsorbents for antibody purification were prepared by conjugating the peptoids to a chromatographic support. The peptoids were conjugated to a chromatographic resins, such as Toyopearl amino AF-650-M, Sepharose or Agarose activated with pendant epoxy, bromoacetyl, tresyl, or bromohydrin groups. The peptoid was dissolved in 80% acetonitrile, 10% methanol, and 10% water at a concentration of 10 mg/mL along with a 10-fold excess of diisopropylethylamine, and incubated with an appropriate amount of resin. The reactions were allowed to proceed overnight with end-over-end agitation at 50°. The resin was then filtered and washed with methanol and water. The collected supernatants and wash fractions were spectrophotometrically analyzed at 280 nm to determine the degree of conjugation relative to the initial amount peptoid in solution. (See Table 6 for representative ligand density and conjugation efficiency).

Figure 3:
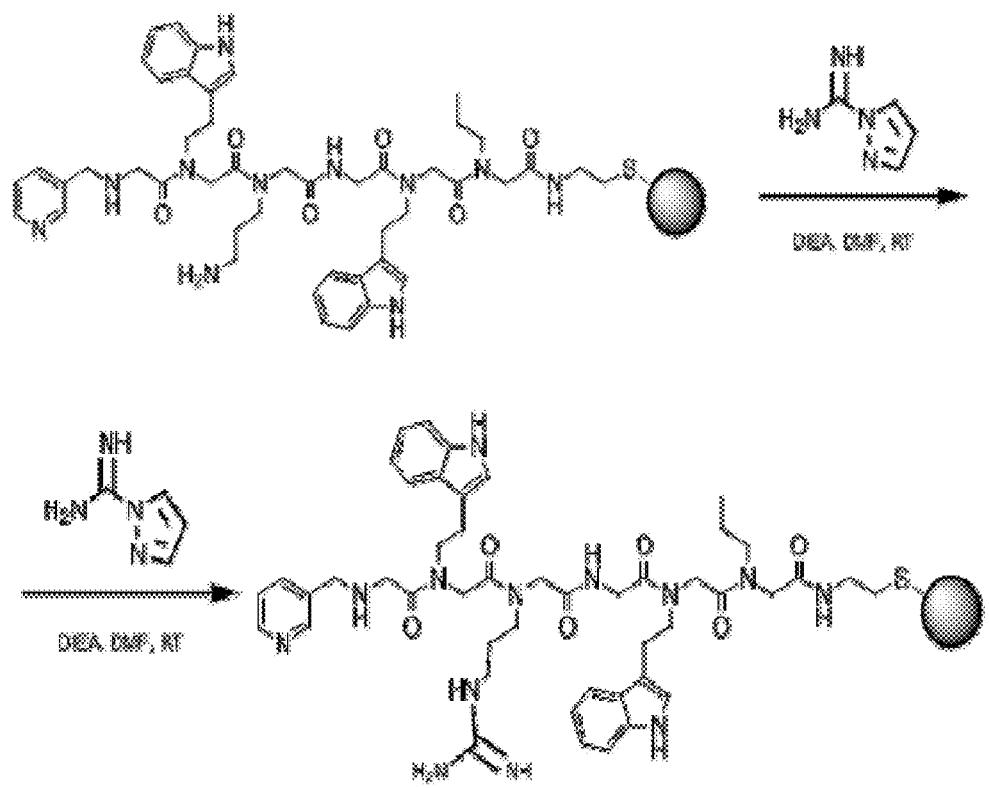
FIG. 3. Conversion of peptoid on chromatographic resin to final affinity ligand.

Following peptoid conjugation to the resin, the primary amino-group of the third residue was convert to a guanidinyl group (FIG. 3). The resin was suspended in dimethylformamide, and 10 equivalents of 1H-pyrazole-1-carboxamidine hydrochloride and diisopropylethylamine were added. The suspension was agitated overnight at room temperature. After incubation, the resin was sequentially washed with dimethylformamide, methanol, and then water. The resins were then stored in 20% methanol/water prior to use. The resulting ligands on the resin are listed in Table 4, where the linker between the resin, R', is either terminated with a cysteine or cysteamine.

TABLE 3

Structures of peptoids from synthesis resin prior to conjugation

| Precursor for Ligand ID# | Structure |
|---|---|
| PV-P-G029 | 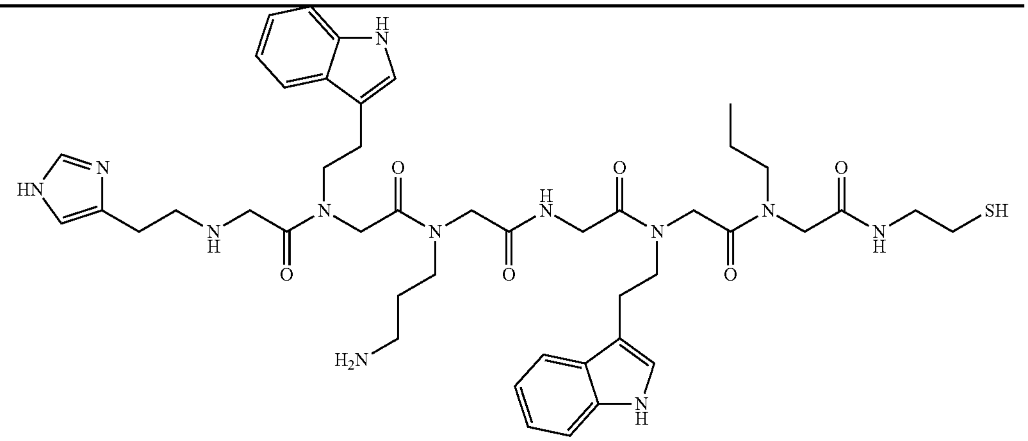 |

TABLE 3-continued

Structures of peptoids from synthesis resin prior to conjugation

| Precursor for Ligand ID# | Structure |
| --- | --- |
| PV-P-G038 | 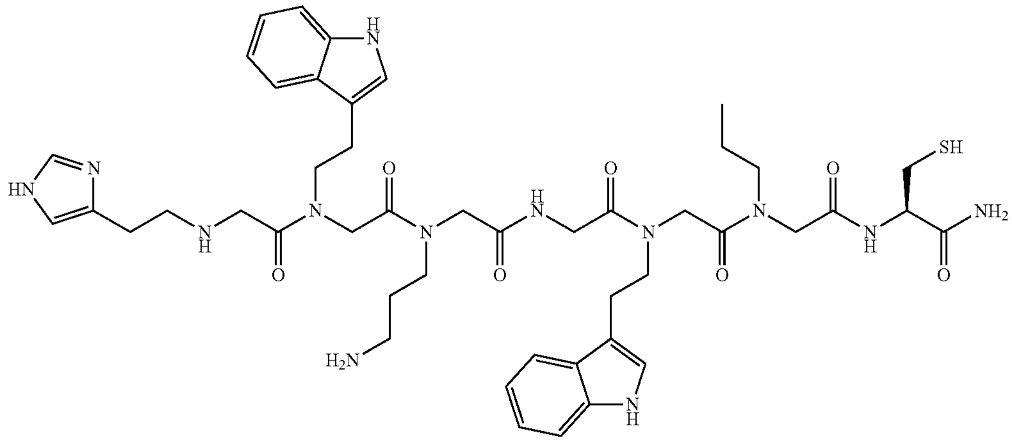 [SMILES: CCCN(CC(=O)N[C@@H](CS)C(N)=O)C(=O)CN(CCc1c[nH]c2ccccc12)C(=O)CNC(=O)CN(CCCN)C(=O)CN(CCc1c[nH]c2ccccc12)C(=O)CNCCc1c[nH]cn1] |
| PV-P-G042 | 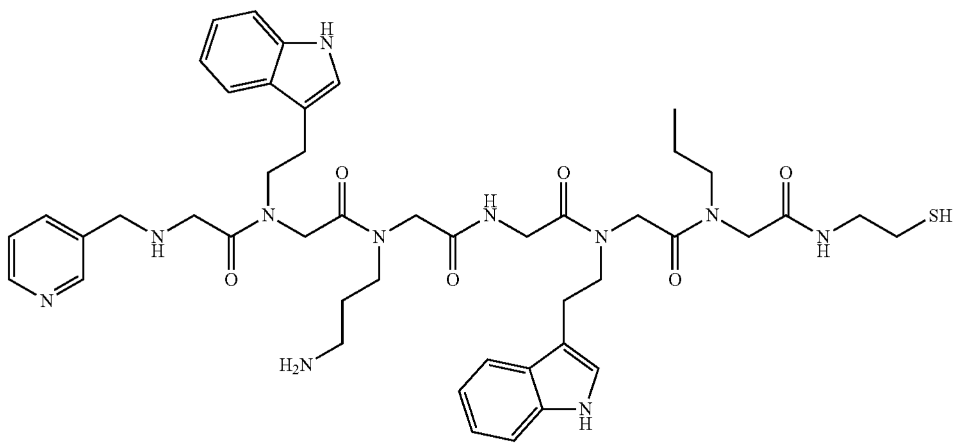 [SMILES: CCCN(CC(=O)NCCS)C(=O)CN(CCc1c[nH]c2ccccc12)C(=O)CNC(=O)CN(CCCN)C(=O)CN(CCc1c[nH]c2ccccc12)C(=O)CNCc1cccnc1] |
| PV-P-G043 | 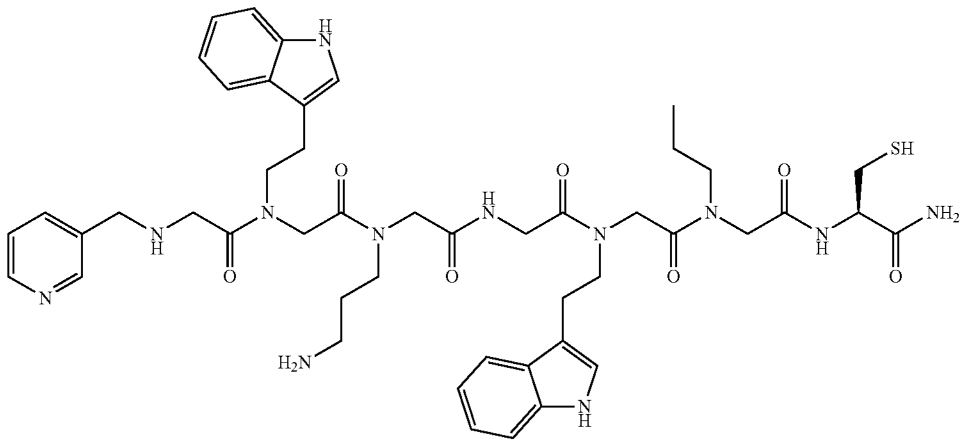 [SMILES: CCCN(CC(=O)N[C@@H](CS)C(N)=O)C(=O)CN(CCc1c[nH]c2ccccc12)C(=O)CNC(=O)CN(CCCN)C(=O)CN(CCc1c[nH]c2ccccc12)C(=O)CNCc1cccnc1] |

TABLE 4

Peptoid ligands used for antibody purification

| ID | PV-P-G029 | PV-P-G038 | PV-P-G042 | PV-P-G043 |
| --- | --- | --- | --- | --- |
| $R^1$ | -3-imidazole | -3-imidazole | -3-pyridyl | -3-pyridyl |
| $R^{1'}$ | —$CH_2CH_2$— | —$CH_2CH_2$— | —$CH_2CH_2$— | —$CH_2CH_2$— |

TABLE 4-continued

Peptoid ligands used for antibody purification

| ID | PV-P-G029 | PV-P-G038 | PV-P-G042 | PV-P-G043 |
|---|---|---|---|---|
| $R^2$ | -3-indole | -3-indole | -3-indole | -3-indole |
| $R^{2'}$ | —CH$_2$CH$_2$— | —CH$_2$CH$_2$— | —CH$_2$CH$_2$— | —CH$_2$CH$_2$— |
| $R^3$ | —NH—(C=NH)—NH2 (guanidyl) | —NH—(C=NH)—NH2 (guanidyl) | —NH—(C=NH)—NH2 (guanidyl) | —NH—(C=NH)—NH2 (guanidyl) |
| $R^{3'}$ | —CH$_2$CH$_2$CH$_2$— | —CH$_2$CH$_2$CH$_2$— | —CH$_2$CH$_2$CH$_2$— | —CH$_2$CH$_2$CH$_2$— |
| $R^4$ | H | H | H | H |
| $R^{4'}$ | N/A | N/A | N/A | N/A |
| $R^5$ | —CH$_2$— | —CH$_2$— | —CH$_2$— | —CH$_2$— |
| $R^{5'}$ | -3-indole | -3-indole | -3-indole | -3-indole |
| $R^6$ | —CH$_2$CH$_2$CH$_3$ | —CH$_2$CH$_2$CH$_3$ | —CH$_2$CH$_2$CH$_3$ | —CH$_2$CH$_2$CH$_3$ |
| $R^{6'}$ | N/A | N/A | N/A | N/A |

TABLE 5

Structures of ligands after conjugation and guanidinylation.

| Ligand ID | Structure |
|---|---|
| PV-P-G029 | 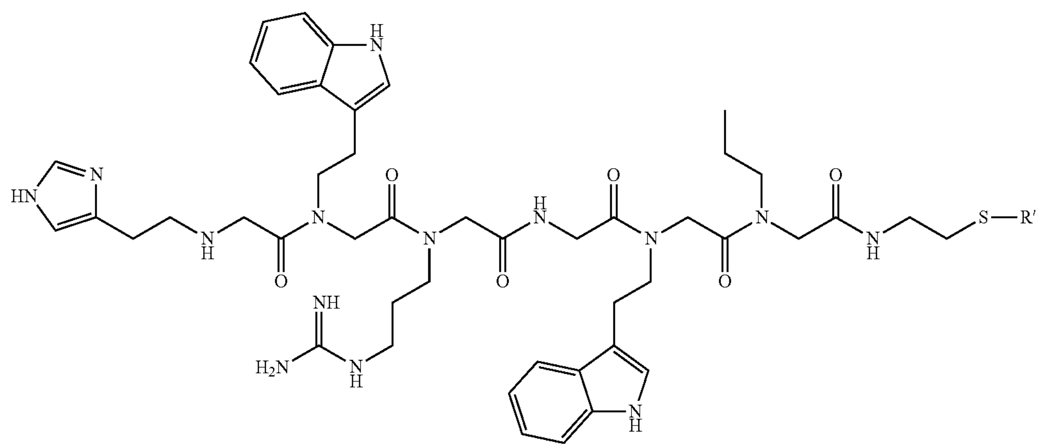 |
| PV-P-G038 | 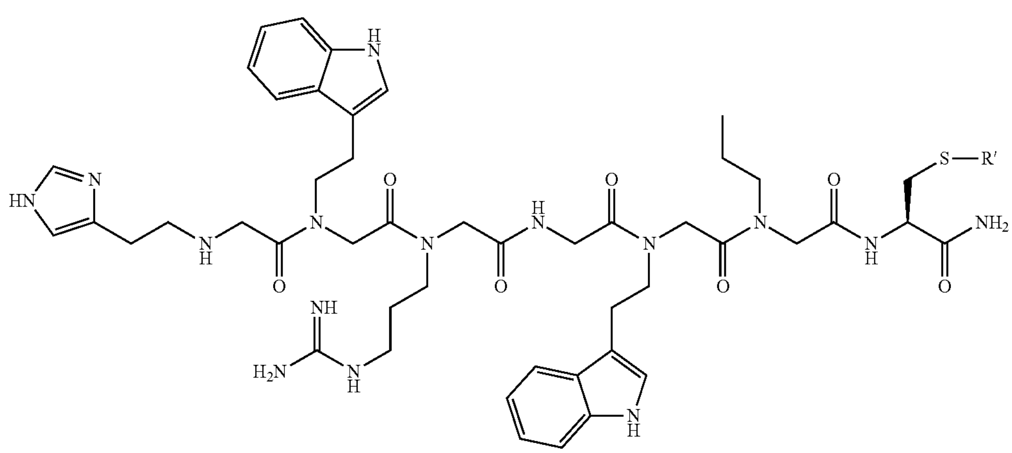 |

TABLE 5-continued

Structures of ligands after conjugation and guanidinylation.

| Ligand ID | Structure |
| --- | --- |
| PV-P-G042 | [chemical structure] |
| PV-P-G043 | [chemical structure] |

TABLE 6

Surface density of peptoid ligands on affinity adsorbents and corresponding values of conjugation efficiency.

| Ligand | Target Ligand Density (mmol Ligand/mL Resin) | Conjugation Efficiency | Actual Ligand density (mmol Ligand/mL Resin) |
| --- | --- | --- | --- |
| PV-P-G029 | 0.05 | 74% | 0.04 |
| PV-P-G038 | 0.07 | 70% | 0.05 |
| PV-P-G042 | 0.1 | 84% | 0.08 |
| PV-P-G043 | 0.05 | 54% | 0.03 |

EXAMPLE 3

Binding of Human Immunoglobulin from PBS in Absence of Other Proteins

Figure 4:
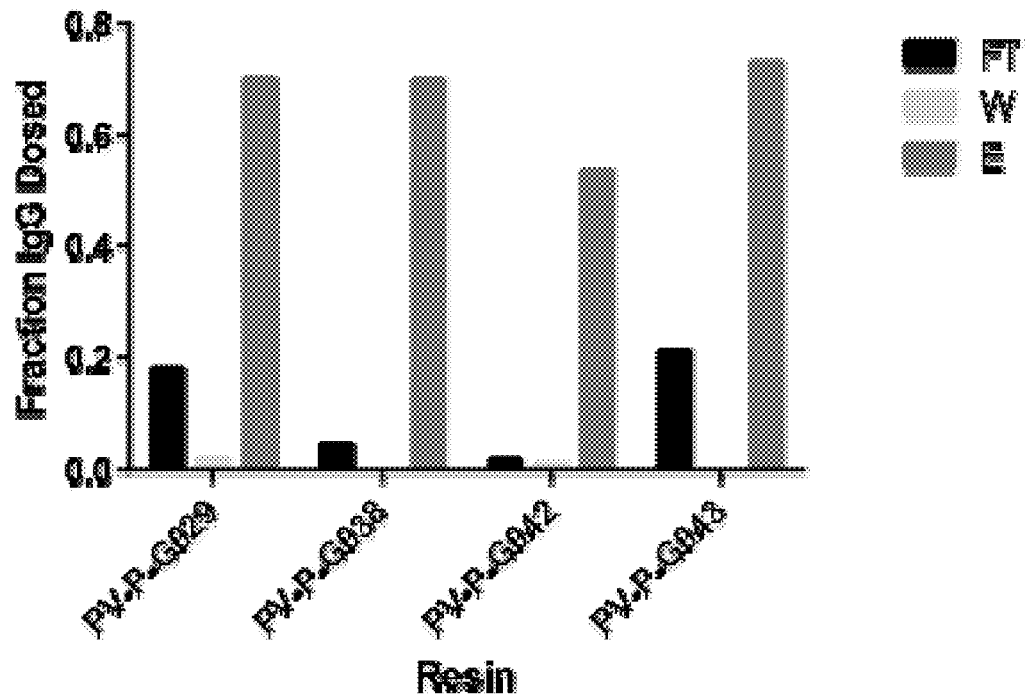
FIG. 4. Batch mode IgG adsorption resins functionalized with different peptoid ligands. IgG in the flow-through fractions (black) indicate the percent hIgG that was not adsorbed to the resin relative to the mass of hIgG loaded. The elution fractions (grey) indicate the percent of hIgG that was bound in PBS and eluted (0.1 M glycine, pH 2.5) relative to the initial concentration of IgG that was loaded. Concentrations of hIgG in all fractions were determined by Bradford assay.

The ability of the peptoid affinity ligands to bind human IgG molecules was tested in batch mode. A 50% slurry of the resin was prepared, of which 100 μl (~50 mg resin) was transferred into a spin column. The resin was washed with 2×200 μL of 0.1 M glycine buffer (pH 2.5), and rinsed with phosphate buffer saline (PBS), pH 7.4 prior to chromatography. Human polyclonal immunoglobulin G (hIgG) was diluted to 0.5 mg/mL with PBS. After draining the resin, the hIgG solution was added to the resin to obtain a ratio of 2 mg hIgG per mL of resin, and mixed vigorously for 5 minutes at room temperature. After incubation, the resin was centrifuged at 500×g for 2 min and the filtrate was collected and labeled as "flow-through" fraction. The resin was washed with 2×200 μL of PBS. Elution buffer (0.1 M glycine, pH 2.5, 200 μL) was added to the resin and mixed vigorously for 5 minutes at room temperature. After centrifugation (500×g for 2 min), the fraction containing the hIgG eluted from the resin was collected and labeled as "eluate". The amount of hIgG in the flow-through and elution fractions was determined via either Bradford or BCA colometric assays. hIgG yields were determined as the ratio of hIgG mass in the elution fraction and hIgG mass in the loading solution (FIG. 4).

EXAMPLE 4

IgG Binding in the Presence of Other Proteins

Figure 5:
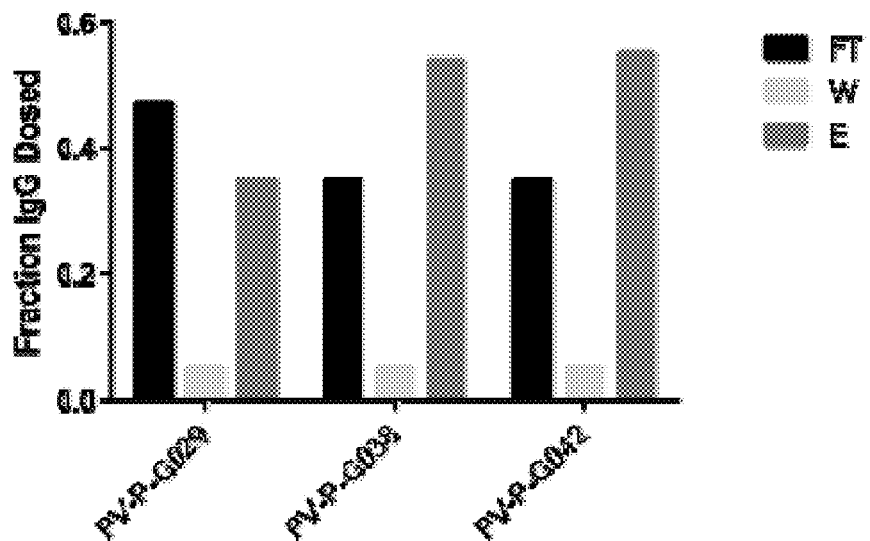
FIG. 5. Batch mode IgG adsorption for resins functionalized with different peptoid ligands in the presence of 0.5 mg/mL bovine serum albumin, 0.5 mg/mL conalbumin, and 0.4 mg/mL lysozyme. A total of 20 mg IgG per mL of resin was loaded for each resin. IgG in the flowthrough fractions (black) indicate the combined percent hIgG (relative to the mass loaded) that was not adsorbed to the resin for two subsequent exposures to 10 mg IgG/mL resin. The elution fractions (grey) indicate the combined percent of hIgG that was eluted from the resins using 0.1 M glycine, pH 4.0 followed by a second elution using 0.1 M glycine, pH 2.5. IgG in the high salt wash (PBS+1 M NaCl) is also shown (light grey). Concentrations of hIgG in all fractions were determined by ELISA.
Figure 6:
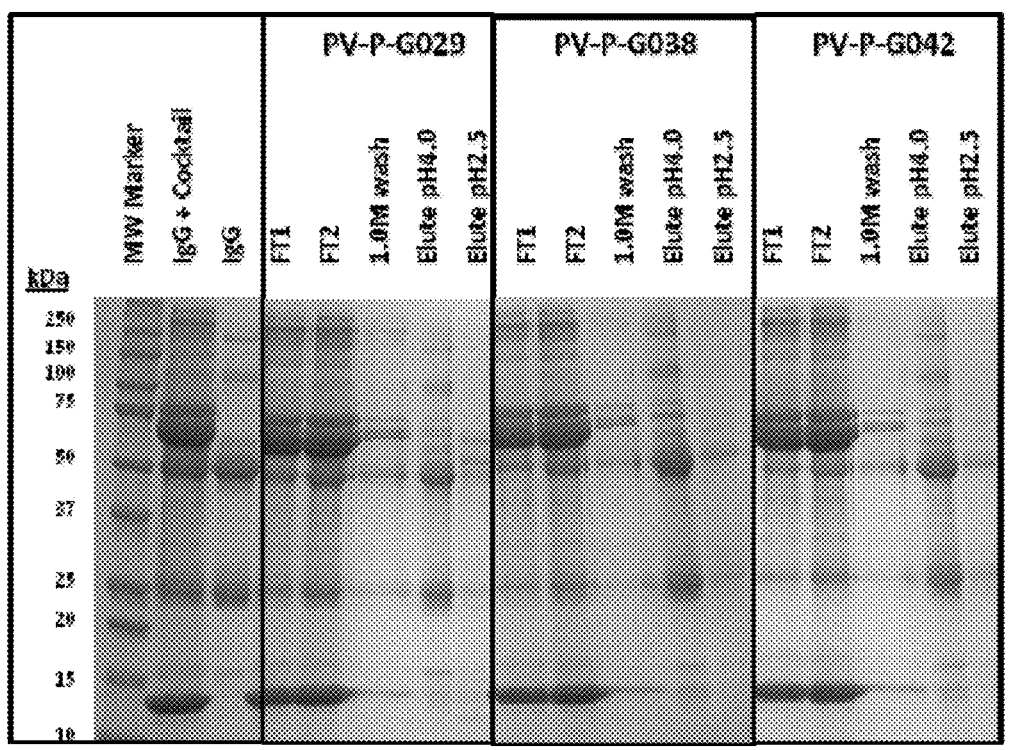
FIG. 6. SDS-PAGE analysis of batch mode IgG adsorption in presence of 0.5 mg/mL bovine serum albumin, 0.5 mg/mL conalbumin, and 0.4 mg/mL lysozyme. The gel was run under reducing conditions and stained with coomassie blue dye. The flowthrough fractions from two subsequent 10 mg IgG per mL resin exposures are shown as FT1 and FT2. The high salt wash (PBS+1 M NaCl) and both the pH 4.0 and pH 2.5 elution fractions are also shown. Purified IgG and the loading material (IgG+Cocktail) are also shown.

The peptoid ligands were further tested for their ability to bind human IgG in the presence of a defined group of competing protein species. The protein cocktail was prepared in PBS and comprised bovine serum albumin (BSA), lysozyme, and conalbumin at the concentration of 0.5, 0.5, and 0.4 mg/mL respectively. Human IgG was spiked in the cocktail to reach a concentration of 0.5 mg/mL. Sodium caprylate and sodium chloride were added to the IgG-spiked cocktail to reach the concentrations of 50 and 250 mM, respectively. Binding assays were carried out in batch mode using spin columns. Approximately 30 mg (wet/drained weight) of fresh resin was transferred into a spin column. Prior to IgG loading, the resins were thoroughly washed with 40 CV of PBS, followed by 20 CV of 0.1 M glycine pH 2.5, and finally re-equilibrated with 40 CV of PBS. The IgG-spiked cocktail was added to the resin at the ratio of 10 mg IgG per mg of wet/drained resin. The mixture was incubated at 21° C. under vigorous shaking for 45 minutes. After incubation, the mixture was centrifuged (1,000×g) for 1 min and the filtrate containing the unbound proteins was collected and labeled as "flowthrough". This process was repeated with additional 10 mg IgG per mL of resin added to the resin, thus totalling 20 mg IgG loaded per mL of resin load. The resin was then washed with 20 CV of PBS followed by a 20 CV high salt wash (PBS+1 M NaCl). Bound protein was eluted from the column using a stepwise elution scheme comprising 20 CV of 0.1 M glycine pH 4.0 followed by 20 CV of 0.1 M glycine pH 2.5. Each elution was performed by incubating the resin in each elution buffer for 10 min under vigorous shaking. The fluid collected by filtration were labeled as "eluate" fractions. The amount of hIgG in each fraction was determined by ELISA. IgG yields were determined as the ratio of the mass of hIgG in the eluted fraction and the mass of the loading solution (FIG. 5). The collected fractions were analysed by SDS-PAGE (in reducing conditions) to evaluate the purity of recovered IgG and hence the adsorbent selectivity (FIG. 6).

EXAMPLE 5

IgG Binding from Conditioned CHO Media

Figure 7:
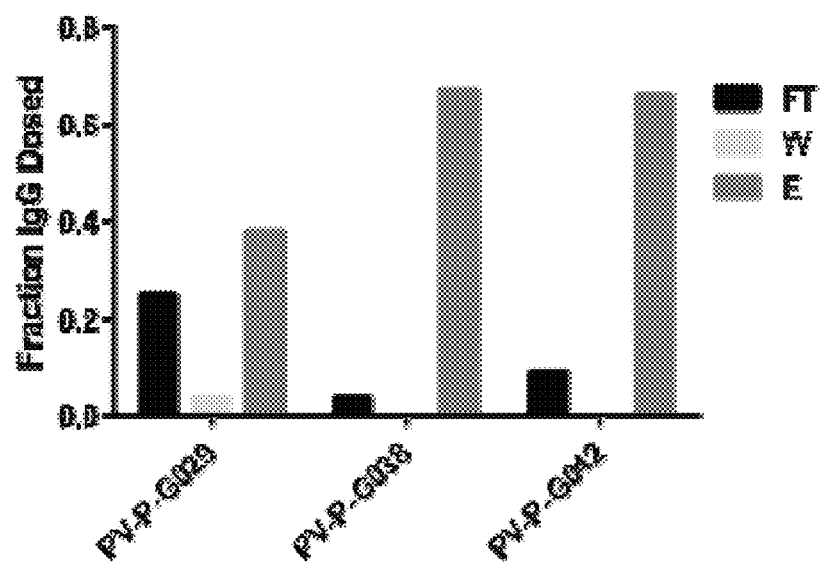
FIG. 7. Batch mode IgG adsorption for resins functionalized with different peptoid ligands from conditioned CHO media containing 1% FBS. Resins were loaded at a ratio of 10 mg IgG per mL of resin. IgG in the flow-through fractions (black) indicate the percent hIgG (relative to the mass loaded) that was not adsorbed to the resin. The elution fractions (grey) indicate the combined percent of hIgG that was eluted from the resins using 0.1 M glycine, pH 4.0 followed by a second elution using 0.1 M glycine, pH 2.5. IgG in the high salt wash (PBS+1 M NaCl) is also shown (light grey). Concentrations of hIgG in all fractions were determined by ELISA.
Figure 8:
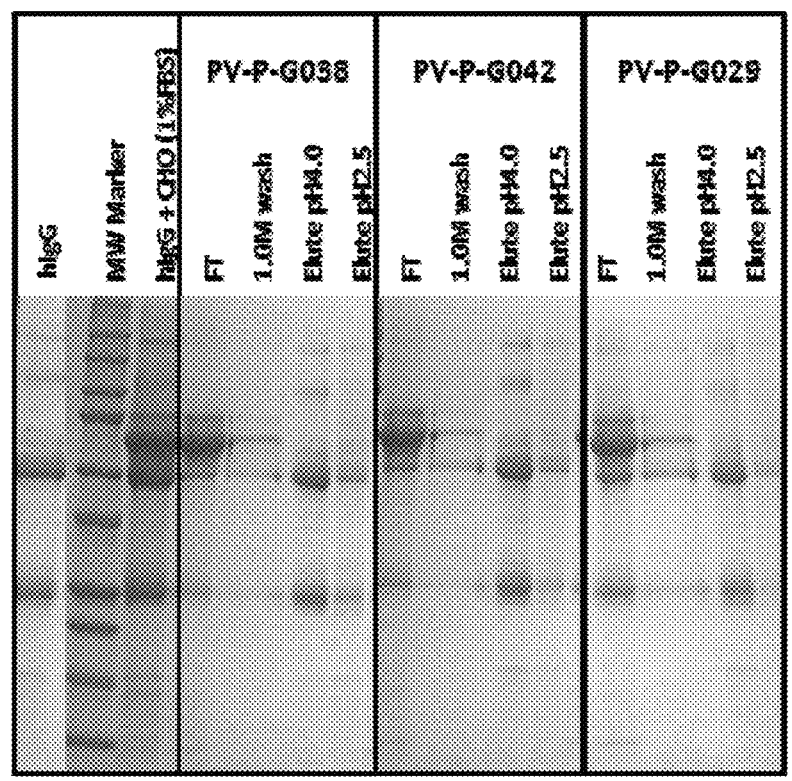
FIG. 8. SDS-PAGE analysis of batch mode IgG adsorption from conditioned CHO media containing 1% FBS. The gel was run under reducing conditions and stained with Coomassie blue dye. The flowthrough fraction (FT) shows the protein that did not bind the resin from a 10 mg IgG per mL resin loading. The high salt wash (PBS+1 M NaCl) and both the pH 4.0 and pH 2.5 elution fractions are also shown. Purified IgG and the loading material (IgG+CHO (1% FBS)) is also shown.

The peptoid ligands were tested for their ability to purify hIgG from conditioned Chinese hamster ovary (CHO) cell culture media. Adherent CHO cells were grown in T-150 flasks, fed with F12K Nutrient Media (containing 1% FBS) at 37° C. with 5% CO2. After 3 days of incubation, the media was harvested from the cells and labeled as "conditioned CHO media", and comprises both residual proteins from the 1% FBS and secreted CHO host cell proteins. Human IgG was spiked into the CHO conditioned media to reach a final concentration of 0.5 mg/mL. Sodium chloride was also added to reach a final concentration of 0.25 M. Binding assays were done in batch mode using spin columns. Approximately 30 mg (wet/drained weight) of fresh resin was transferred into a spin column. Prior to IgG loading, the resins were thoroughly washed with 40 CV of PBS, followed by 20 CV of 0.1 M glycine pH 2.5, and finally re-equilibrated with 40 CV of PBS. The IgG-spiked conditioned CHO media was added to the resin at a ratio of 10 mg IgG per mg of wet/drained resin. This mixture was incubated at 21° C. under vigorous shaking for 45 minutes. After incubation, the suspension was centrifuged (1,000×g, 1 min) and the filtrate containing the unbound proteins was collected (flowthrough fraction). The resin was then washed with 20 CV of PBS and 20 CV of 1 M NaCl in PBS. Bound protein was eluted from the column using a stepwise elution scheme consisting of 20 CV of 0.1 M glycine pH 4.0 followed by 20 CV of 0.1 M glycine pH 2.5. Each elution was performed by incubating the resin in each elution buffer for 10 min under vigorous shaking. The fluid collected by filtration were labeled as "eluate" fractions. The amount of hIgG in each fraction was determined by ELISA. IgG yields were determined as the ratio of the mass of hIgG in the eluted fraction and the mass of the loading solution (FIG. 7). The collected fractions were analysed by SDS-PAGE (in reducing conditions) to evaluate the purity of recovered IgG and hence the adsorbent selectivity (FIG. 8).

The foregoing is illustrative of the present invention, and is not to be construed as limiting thereof. The invention is defined by the following claims, with equivalents of the claims to be included therein.

That which is claimed is:
1. A compound consisting of:

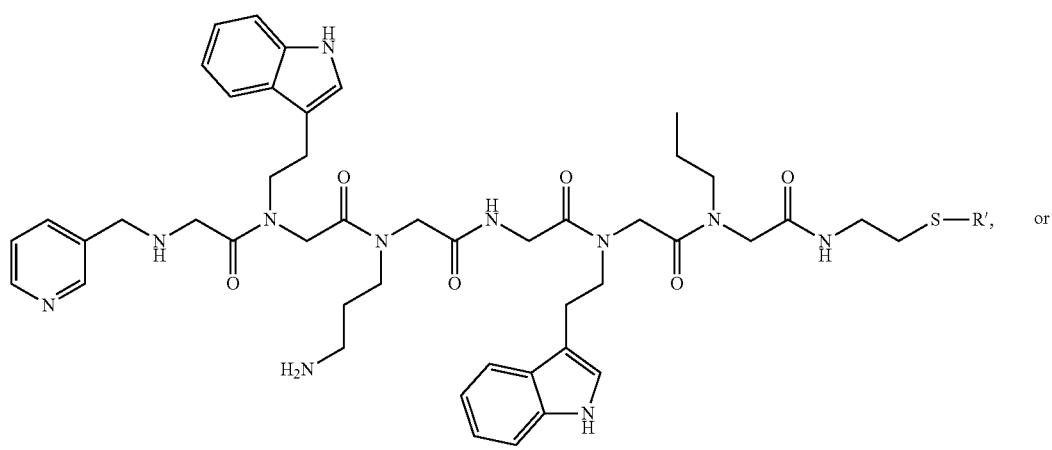

PV-P-G042

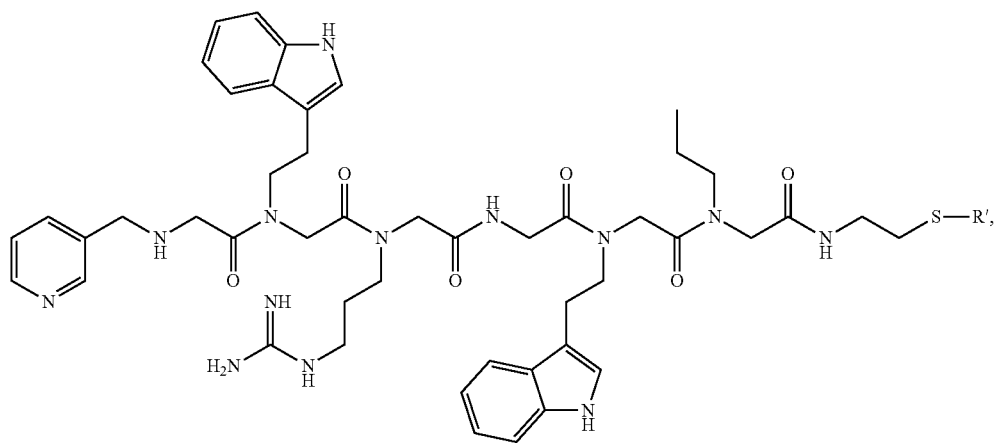

where R' is H or a solid support, wherein the solid support is configured to immobilize the compound in an ex vivo application.

2. The compound of claim 1, wherein the solid support comprises a chromatographic support.

3. The compound of claim 1, wherein said solid support comprises a particle, wherein the particle is porous and hydrophilic.

4. The compound of claim 1 herein said solid support comprises an inorganic material.

5. A compound consisting of:

PV-P-G043

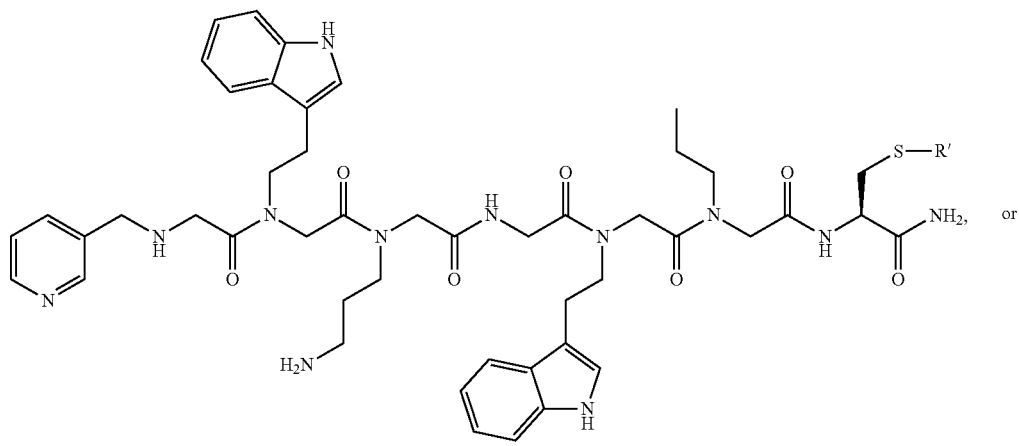

or

PV-P-G043

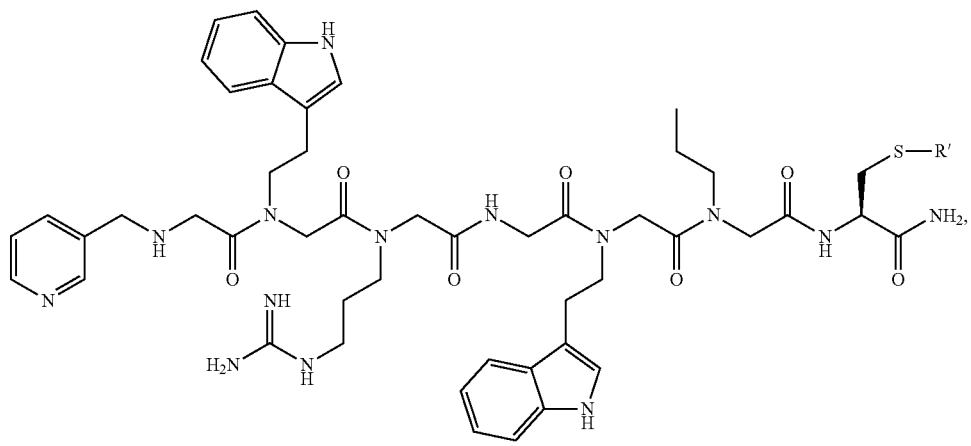

where R' is H or a solid support, wherein the solid support is configured to immobilize the compound in an ex vivo application.

6. The compound of claim 5, wherein the solid support comprises a particle, wherein the particle is porous and hydrophilic.

7. The compound of claim 5, wherein the solid support comprises an inorganic material.

8. The compound of claim 5, wherein the solid support comprises a chromatographic support.

* * * * *